United States Patent
Dordick et al.

(10) Patent No.: US 7,172,682 B2
(45) Date of Patent: Feb. 6, 2007

(54) ENZYME IMMOBILIZATION FOR ELECTROOSMOTIC FLOW

(75) Inventors: Jonathan S. Dordick, Schenectady, NY (US); Moo-Yeal Lee, Troy, NY (US); Aravind Srinivasan, Troy, NY (US); Bosung Ku, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 444 days.

(21) Appl. No.: 10/351,976

(22) Filed: Jan. 24, 2003

(65) Prior Publication Data

US 2007/0000781 A1    Jan. 4, 2007

(51) Int. Cl.
C07K 17/14 (2006.01)
(52) U.S. Cl. .............. 204/450; 204/600; 435/175; 435/176
(58) Field of Classification Search .............. 204/451, 204/450, 600; 435/174–182; 422/100
See application file for complete search history.

(56) References Cited

U.S. PATENT DOCUMENTS

| 3,650,900 | A | | 3/1972 | Levin et al. | |
|---|---|---|---|---|---|
| 5,181,999 | A | | 1/1993 | Wiktorowicz | |
| 5,885,470 | A | * | 3/1999 | Parce et al. | 216/33 |
| 6,403,368 | B1 | * | 6/2002 | Jan et al. | 435/287.2 |
| 6,582,969 | B1 | * | 6/2003 | Wagner et al. | 436/518 |
| 2002/0185184 | A1 | | 12/2002 | O'Connor et al. | |
| 2004/0121491 | A1 | * | 6/2004 | Marchand-Brynaert et al. | 436/527 |

FOREIGN PATENT DOCUMENTS

| EP | 0 452 055 B1 | 1/1995 |
|---|---|---|
| GB | 1 274 869 | 5/1972 |
| JP | 11-164687 | 6/1999 |
| WO | WO/01/14437 A1 | 8/2000 |
| WO | WO 00/62051 | 10/2000 |

OTHER PUBLICATIONS

Miller, Scott A., and Martin, Charles R., "Controlling the rate and direction of electroosmotic flow in template-prepared carbon nanotube membranes", Mar. 22, 2002, Journal of Electroanalytical Chemistry, vol. 522, pp. 66-69.*

Drott, J., et al., "Porous silicon as the carrier matrix in microstructured enzyme reactors yielding high enzyme activities," *J. Micromech. Microeng.*, 7:14-23 (1997).

(Continued)

*Primary Examiner*—Nam Nguyen
*Assistant Examiner*—Anthony Fick
(74) *Attorney, Agent, or Firm*—Carolyn S. Elmore; Darlene A. Vanstone; Elmore Patent Law Group, P.C.

(57) ABSTRACT

Disclosed herein is a method and apparatus of immobilizing a biocatalyst on a microfluidic biochip for conducting reactions in the presence of electroosmotic flow. The biochip includes a polymer on its microfluidic flow surfaces, wherein the polymer includes a first substituent selected from ionic groups of the same polarity or precursors thereof, a second substituent that is a hydrophobic group, and a third substituent comprising an immobilized biocatalyst-or precursor thereof. The biochip can be used to conduct multiple sequential biocatalyzed reactions in the presence of electroosmotic flow.

36 Claims, 10 Drawing Sheets

OTHER PUBLICATIONS

Haswell, S.J. and Skelton, V., "Chemical and biochemical microreactors," *Trends in Analytical Chemistry*, 19(6): 389-395 (2000).

Laurell, T., et al., "Silicon wafer integrated enzyme reactors," *Biosensors & Bioelectronics*, 10: 289-299 (1995).

Liu, Y., et al., "Dynamic coating using polyelectrolyte multilayers for chemical control of electroosmotic flow in capillary electrophoresis microchips," *Analytical Chemistry*, 72(24):5939-5944 (2000).

Nagy, G., et al., "Amperometric microcell for enzyme activity measurements," *Analytical Chemistry*, 70(10):2156-2162 (1998).

Park, C.B. and Clark, D.S., "Sol-gel encapsulated enzyme arrays for high-throughput screening of biocatalytic activity," *Biotechnology and Bioengineering*, 78(2): 231-235 (2002).

* cited by examiner

ENZYME IMMOBILIZATION FOR ELECTROOSMOTIC FLOW

GOVERNMENT SUPPORT

The invention was supported, in whole or in part, by grants from the Defense Advanced Research and Projects Agency, the Biotechnology Research and Development Corporation and the National Science Foundation under grant number BES-0118820. The Government has certain rights in the invention.

BACKGROUND OF THE INVENTION

Microfluidics is the field of microscale fluid flow and control, typically through microscale fluid control features constructed on a substrate such as a glass chip. These devices can be used to manipulate liquid chemical and biological samples in order to conduct analysis, perform synthetic reactions, and the like.

A motive force often used in microfluidics is a phenomenon known as electroosmotic flow (EOF). EOF depends strongly on various aspects of charge mobility in these systems, and in particular, depends on having a high density of ionic groups of the same polarity on the walls or flow surfaces of a microfluidics component. For example, a typical microfluidics feature is a microchannel etched in a glass substrate. The interior surface of the channel is treated to expose free silanol groups, which can then be deprotonated to provide siloxide anions. A voltage is applied across the flow direction of the channel causing solvated counterions of the charged groups on the channel walls to move. Because the dimensions of a microfluidic channel are small, the layer of counterions at the flow surface contact a significant portion of the fluid in the channel. Thus, when the counterion layer moves, the entire volume of the channel moves nearly simultaneously, a mechanism known as "plug flow". For many applications, plug flow is advantageous because it means that the components of a particular volume portion of the flow travel together, and are not spread out as they would be in a conventional pressure driven flow. Thus, on a microfluidics chip, precise volumes can be delivered from one location to another with a high degree of control.

Many features of a macroscale laboratory can thus be miniaturized using microfluidics, allowing significant reductions in the amount of costly, rare, or hazardous materials that are used. For example, microfluidics has the potential to make efficient use of biomolecules such as enzymes or catalytic antibodies, which are typically expensive or difficult to prepare in large quantities. It is particularly desirable that these molecules be reusable or recoverable, for example, by immobilizing them to a solid support, in order to further limit the quantities that are required.

A significant problem that must be solved, however, is the difficulty of immobilizing biomolecules with high biological activity while simultaneously maintaining acceptable EOF capability.

For example, enzymes have been attached to glass chips by covalent attachment to free silanol groups on the glass surface. However, the high pH necessary to provide the charged siloxide anions significantly decreases the stability and catalytic activity of enzymes. Another attempt functionalized the silanol groups with a linker group ending in an amine, which can then be covalently attached to the enzyme. However, this leads to a reduction in the number of available siloxide groups at the surface, and further, shields the groups that are present from the flow, resulting in poor EOF characteristics.

Other attempts have been made to provide polymers that specifically enhance EOF, for example, by using a charged polymer such as dextran sulfate. These polymers, however, are dynamically unstable coatings, i.e., are not substantially adhered, and so are eventually washed away by the flow. Furthermore, they are not easily functionalized with biocatalysts such as enzymes, and they do not maintain the catalytic activity of enzymes.

High enzyme activity can be maintained by encapsulating and/or covalently attaching enzymes to matrices, such as solgels, but such matrices typically fill the entire microfluidic channel, providing a severe impediment to fluid flow. Furthermore, many other examples of polymers exist to immobilize enzymes with high activity, but they are not designed to support EOF.

Therefore, there is a need to immobilize biomolecules on a microfluidics apparatus, while simultaneously maintaining high biological activity and high EOF capability.

SUMMARY OF THE INVENTION

It has now been found that certain polymers containing both ionic groups and hydrophobic groups can be substantially adhered to microfluidic channels and can be used to simultaneously immobilize biocatalysts with good catalytic activity while supporting electroosmotic flow.

One embodiment of the invention is method of immobilizing a biomolecule in the presence of electroosmotic flow. One step is providing a microfluidic biochip. The biochip includes a microfluidic component comprising a flow surface; at least two electrodes whereby an electroosmotic flow can be generated at the flow surface; and an immobilizing polymer that is substantially adhered to the flow surface. The polymer includes a first substituent selected from ionic groups of the same polarity and covalent precursors of the ionic groups, wherein the first substituent is optionally a biomolecule immobilizing group. The polymer includes a second substituent that is a hydrophobic group. The polymer optionally includes a third substituent that is a biomolecule-immobilizing group. Between the first substituent and the optional third substituent, the polymer includes at least one substituent that is a biomolecule-immobilizing group. Another step of the method is applying a motive force selected from pressure, electroosmotic force, capillary action, and centrifugal force, thereby generating flow. Yet another step is directing a biomolecule from a source to the polymer by employing the flow. An additional step is reacting the biomolecule with the biomolecule-immobilizing group under suitable reaction conditions, whereby the biomolecule is immobilized.

Another embodiment of the invention is the biochip, wherein the substituents of the immobilizing polymer include a first substituent selected from ionic groups of the same polarity and covalent precursors of the ionic groups; a second substituent that is a hydrophobic group; and a third substituent comprising an immobilized biomolecule.

Another embodiment of the invention is a method for conducting one or more reactions by using the biochip. The biochip additionally includes at least one reservoir, wherein the reservoir contains a starting reactant. All the microfluidic components are in microfluidic communication. The substituents of the immobilizing polymer include ionic groups of the same polarity; a hydrophobic group; a first immobilized biomolecule; and optionally a second, chemically distinct immobilized biomolecule; A step of the method is applying a voltage to the electrodes, thereby generating electroosmotic flow. Another step is directing the reactant from the reservoir to the first biomolecule by employing the electroosmotic flow, then reacting the first reactant with the first biomolecule under suitable reaction conditions, thereby producing a first reaction product. Another step is optionally contacting the first product with the second biomolecule, if present, and reacting the first product with the second biomolecule under suitable reaction conditions, thereby producing a second reaction product.

The invention can be used to immobilize biomolecules on a microfluidics biochip to conduct reactions. The invention retains the activity of the biomolecules while simultaneously supporting EOF. Also, the invention allows multiple reactions using catalytically distinct biomolecules. Furthermore, the invention allows sequential reactions using catalytically and spatially distinct immobilized biomolecules. Thus, using the invention, a wide array of sequential, stepwise reactions can be conducted with high activity while minimizing the use of costly or dangerous reactants.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5B graphs poly(p-cresol) production in a three enzyme system immobilized in distinct locations on a PDMS biochip (filled circles) compared to a solution control (open circles) and.

DETAILED DESCRIPTION OF THE INVENTION

Figure 1:
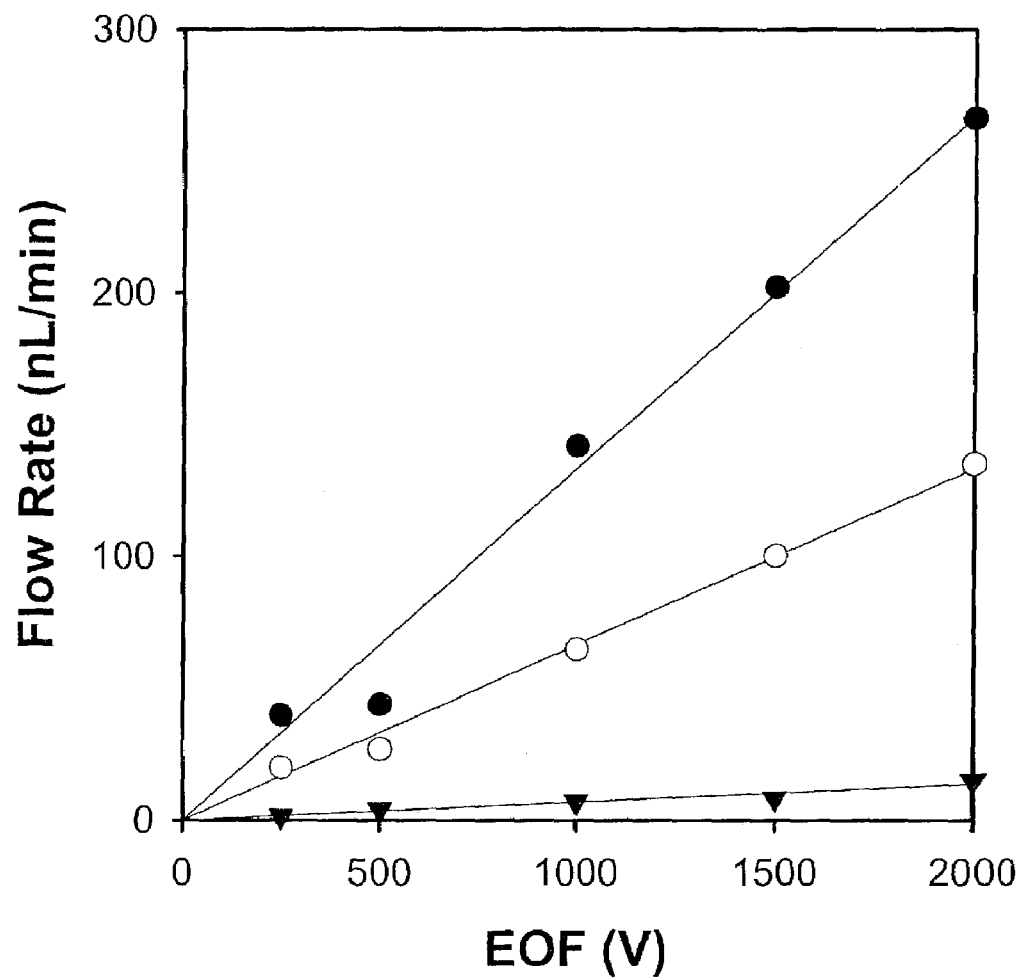
FIG. 1 graphs enhanced electroosmotic flow versus voltage for PMA-OL (poly (maleic anhydride)-alt-α-olefin) coated channels of the invention (open circles) compared glutaraldehyde-coated control channels (solid triangles), with reference to glass EOF control channels (solid circles).

The invention is generally directed to methods of immobilizing biomolecules on a microscale device using an immobilizing polymer. In particular, the invention is directed to immobilizing biomolecules in microfluidic channels, using an immobilizing polymer that simultaneously maintains good biological activity of the biomolecule and good EOF characteristics.

A microfluidic device is a system of microscale fluid control components, such as channels, reservoirs, junctions such as T-junctions, and the like. Typically, these components are incorporated into a single solid substrate, for example, by chemically etching channels and reservoirs into the surface of a chip, e.g., a glass microscope slide, a polymer slab, a silicon wafer, and the like. These features can be made in such solid substrates by other techniques known to the art, for example, precision mechanical machining, laser machining, polymer molding from a machined or etched master, and the like.

The cross-sectional area of a microfluidic channel is less than 0.1 mm$^2$, generally less than 0.05 mm$^2$, more preferably less than 0.025 mm$^2$, and most preferably about 0.003 mm$^2$. The length of a microfluidic channel can be at a much larger scale, for example, a single channel could run up to the length of the substrate, e.g. almost 75 mm on a standard microscope slide, or a channel could loop back and forth on a chip, becoming many times longer than the chip itself. One or more reservoirs are typically connected to microchannel, e.g., to supply buffer solution, reactant solution, to collect products or waste, and the like. Fluid flow in a microfluidic chip can be generated by applying a motive force, for example, pressure, electroosmotic force, capillary action, centrifugal force, and the like. Preferably, the force used is electroosmotic. The biochip typically includes, or is used in combination with, a plurality of electrodes, i.e., at least two, which can be used to apply a voltage for causing EOF.

The ease of generating EOF in a microchannel depends on the number of ionic groups attached to the interior flow surface of the microchannel. When a voltage is applied to electrodes at opposite ends of a channel, negatively charged ions tend to flow to the anode and positively charged ions tend to flow to the cathode. In a channel designed for EOF, the ionic groups attached to the flow surface cannot move. However, the dissolved counterions of the ionic groups can move, and cause the surrounding solvent to move, resulting in EOF.

The rate of fluid flow is ($V_{EOF}$) is affected by several factors (Eq. 1), where E is the electric field (equal to the voltage divided by the distance between the electrodes for microchannels of uniform resistance per unit length), $\epsilon$ is the relative permittivity of liquid, $\epsilon_0$ is the permittivity of free space, $\zeta$ is the zeta potential of the microchannel/liquid interface and $\eta$ is the liquid viscosity (Fletcher, PDI; Haswell, S J; Paunov, V N. *Analyst*, 1999, 124, 1273–1282).

$$V_{EOF} = -\frac{E\varepsilon\varepsilon_0\zeta}{\eta} \quad (1)$$

The sign of Eq 1 indicates the charge of the ionic groups attached to the channel flow surface, i.e. when the channel wall is negatively charged, the ζ-potential is negative, the diffuse charge in the liquid is positive (i.e., due to the positive counterions of the channel wall negative ions) and the liquid flows towards the cathode.

The microfluidic biochip can be made of any material, for example, glass, ceramics, polymers, silicon wafers, metals, and the like, in which microfluidic features can be fabricated. The microfluidic biochip can be a solid slab of a relatively hydrophobic polymer (distinct from the immobilizing polymer) that is readily coated by hydrophobic groups in the immobilizing polymer. For example the biochip can be made of polydialkyl siloxanes such as polydimethyl siloxane (PDMS), polyalkylenes such as polyethylene and polypropylene, polystyrenes, polyvinyl alcohol alkyl ethers, polyacrylate alkyl esters, and the like.

Alternatively, the microfluidic biochip is made of a material that has groups on its surface that are reactive, or can be made reactive, whereby the immobilizing polymer can be covalently attached to the flow surface. For example, a biochip made out of glass possesses —Si—O— groups, which can be treated to expose reactive siloxide anion or silanol surface groups that can react with the immobilizing polymer or with a linker that reacts with the immobilizing polymer. For example, siloxide anion groups on a glass surface can be reacted with a linker, e.g., aminopropyl triethoxysilane (APTES), thus covering the surface with amino groups:

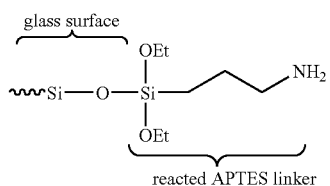

A which can be reacted with the immobilizing polymer. For example, in FIG. 7A (step 3), a maleic anhydride moiety of the immobilizing polymer reacts with the amino group of the APTES that is bound to the glass surface. Subsequently (step 4), the carboxyl group thus released, or another maleic anhydride group (as shown) reacts with an amine on an enzyme (filled circle), thus immobilizing the enzyme. The surfaces of other substrates can be functionalized similarly, for example, surface —CO$_2$CH$_3$ groups on a polymethyl methacrylate substrate could be treated to expose carboxylates, —OH groups in a phenol-formaldehyde substrate can be converted to phenolate anions, and the like.

The "immobilizing polymer" is a multifunctional, substituted polymer that is coated on, or exposed at, a flow surface of the biochip. Through its substituents, the immobilizing polymer can simultaneously provide four functions: biomolecule immobilization, maintenance of biomolecule activity, support of EOF characteristics, and substantial adherence of the polymer to the flow surface of the biochip. The immobilizing polymer contains at least two substituents that can perform these four functions. Preferred polymers possess simple polymer structural chemistry, such as a copolymer with the minimum set of substituents necessary to achieve multiple functions, e.g., a minimal set can be an ionic group (or precursor thereof) and a hydrophobic group. For example, an immobilizing polymer can be substituted with carboxylate and a C24 alkyl chain. The carboxylate can immobilize an enzyme by forming an amide bond and can support EOF through its negative charge, while the alkyl chain can help to maintain the enzyme's activity and can help to adhere the polymer to a hydrophobic microchannel wall through hydrophobic interactions. Alternatively, adherence to the microchannel wall can be provided through the carboxylate, either through ionic association with ionic groups on the microchannel wall or through creation of a covalent bond to the wall. An immobilizing polymer can also contain more than two substituents to perform the four functions, for example, a polymer could have a sulfonate for EOF, a carboxylate or thiol for enzyme immobilization, and a hydrophobic group for enzyme stability and adherence to the surface.

Substituents that support EOF are ionic substituents (or precursors thereof) that are the same polarity. For example, ionic groups can include negatively charged groups such as carboxylate, carbamate, sulfate, thiosulfate, sulfonate, phosphate, phosphonate, and hydroxyl. Alternatively, ionic groups include carboxylate, carbamate, sulfate, and hydroxyl. Preferably, negatively charged ionic groups are carboxylates.

In an alternative embodiment, ionic groups that are positively charged are used. For example, positive ionic groups can be ammonium, phosphonium, and sulfonium groups, optionally substituted with one or more groups selected from C1–C8 alkyl and aryl. Alternatively, positive ionic groups are selected from ammonium groups optionally substituted with C1–C4 alkyl groups. Preferably, positively charged ionic groups are ammonium groups.

Precursors of ionic groups are uncharged groups that can be reacted under appropriate reaction conditions to produce an ionic group, for example, an ester can be hydrolyzed to produce a carboxylate anion. Precursors of ionic groups can include optionally substituted alkyl esters, acids, amides, alkyl anhydrides, cyclic anhydrides, and aryl esters of ionic groups. Alternatively, precursors of ionic groups include optionally substituted alkyl esters, alkyl anhydrides, amides, and cyclic anhydrides. More preferably, precursors are alkyl esters, alkyl anhydrides, or cyclic anhydrides. Most preferably, a precursor is derived from a maleic anhydride group.

Substituents that are biomolecule-immobilizing groups are those that react to form a covalent bond with the biomolecule while maintaining some biological activity. Biomolecule-immobilizing groups can be ionic groups or precursors thereof, such as carboxyl or an anhydride, or can be other groups separate from the ionic groups used to support EOF. Biomolecule immobilizing groups include aldehydes, amines, alcohols, acid halides, alkyl halides, photoprecursors to radicals such as diazo and substituted diazenes, carboxyls, esters, alkyl anhydrides, cyclic anhydrides, thiols, disulfides, and the like. Alternatively, a biomolecule immobilizing group is selected from aldehyde, amine, carboxyls, esters, alkyl anhydrides, cyclic anhydrides, thiols, and disulfides. More preferably, a biomolecule immobilizing group is selected from amines, carboxyls, esters, alkyl anhydrides, cyclic anhydrides, and thiols. Most preferably, a biomolecule immobilizing group is a carboxyl or a cyclic anhydride, for example, maleic anhydride that is part of the polymer backbone.

Substituents that maintain the biological activity of an immobilized biomolecule include hydrophobic groups. A hydrophobic group, as the term is used herein, means a group which, as a separate entity, is more soluble in octanol than water. For example, the octyl group (C8H17) is "hydrophobic" because its parent alkane, octane, has greater solubility in octanol than in water. Specific examples of suitable hydrophobic groups include n-hexyl, n-heptyl, n-octyl, n-nonyl, n-decyl, n-undecyl, n-dodecyl, n-tetradecyl, n-octadecyl, 2-ethylhexyl, 3-propyl-6-methyl decyl, phenyl, (Para n-dodecyl)phenyl, naphthyl, anthracyl, 3-cholesteryl, and the like. The hydrophobic substituent can be an alkyl, cycloalkyl, aliphatic, cycloaliphatic, non-aromatic heterocyclic, aryl, or heteroaryl group, or combinations thereof. The hydrophobic substituents can be the same, for example, all n-C18, or different, such as a range, for example, C24 through C28, or a mixture of structural isomers, for example, branched and linear C16, or mixtures of different groups, such as alkyl and aromatic, and the like. For example, a hydrophobic group can be C8–C30 aliphatic, polycyclic aliphatic, polycyclic aryl, or polycyclic heteroaryl, or a C8–C30 alkyl optionally interrupted or substituted by, for example, a heteroatom, a cycloaliphatic, aryl, or heteroaryl group, and the like. Alternatively, a hydrophobic substituent is an optionally substituted C8–C30 alkyl, polycyclic alkyl, polycyclic aryl, or polycyclic heteroaryl. Preferably, a hydrophobic substituent is a C8–C30 alkyl, and most preferably, a C12–C28 alkyl.

Substituents that substantially adhere the immobilizing polymer to the biochip are those that can create strong noncovalent or covalent interactions between the polymer and the biochip. "Substantially adhere" means that the polymer is not washed away during normal operation of the biochip. For example, hydrophobic substituents can cause substantial adherence to a hydrophobic microchannel wall through hydrophobic interactions, e.g., between octadecyl groups and a polydimethyl siloxane wall. In another example, ionic substituents can cause substantial adherence to a ionic microchannel wall through electrostatic interactions, e.g., between tetraalkyl ammonium cations and siloxide wall anions. In yet another example, a group can form a covalent bond with a microchannel wall, e.g, an ionic group such as a carboxyl can form a covalent bond with a channel surface functionalized with an amine as in structure A. Preferably, the immobilizing polymer is adhered to the wall through hydrophobic interactions or through covalent interactions. More preferably, the immobilizing polymer is substantially adhered through covalent interactions. Most preferably, the immobilizing polymer is covalently attached to the microchannel wall through a linker containing an amide bond, e.g., an amide bond formed between a carboxylate on the polymer and an amine on the linker. In a particularly preferred embodiment, the immobilizing polymer is covalently attached to a glass microchannel wall through a linker represented by structure B:

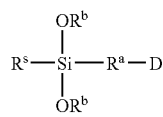

B wherein $R^s$ represents a surface —Si—O— group on the glass microchannel, $R^a$ is a C1–C8 alkylene chain; each $R^b$ is independently a C1–C4 alkyl group; and D represents an amide bond to the immobilizing polymer. For example, amide D can be formed by amidation of a group on the polymer, for example, an acyl halide, an ester, or an anhydride. For example, if the polymer is derived from a maleic anhydride copolymer, amide D can be formed by amidation of one of the maleic anhydride groups on the polymer.

In another alternative, the microfluidic biochip is made of the immobilizing polymer itself, and is thus effectively "substantially adhered" to itself by virtue of being a solid slab.

The immobilizing polymer itself, i.e, prior to reaction with a biocatalyst or adherence to a biochip, can be represented as a copolymer of monomers, wherein the collective substituents of the monomers perform the four functions discussed above. As used herein, a copolymer involves a combination of monomers wherein at least one of each monomer are present in the resulting polymerized polymer in any order. "Can be represented" means that the monomers are the hypothetical monomers that describe the repeat units of the polymer, not necessarily the actual monomer used to make the polymer (i.e. acetylene is the hypothetical monomer of polyacetylene, which can also be made from cyclooctatetraene). The polymer could be made from a single monomer that has appropriate substituents, for example, 2-octadecyl acrylate.

More preferably, the immobilizing polymer can be represented as copolymer of a monomer with an ionic group, e.g., carboxylate, and a monomer with a hydrophobic group, e.g., C16 alkyl. Even more preferably, the immobilizing polymer can be represented as a copolymer of ethylenically unsaturated monomers, e.g., acrylic acid and 1-octadecene. For example, an immobilizing polymer can be represented as a copolymer including a first monomer such as acrylic acid, itaconic anhydride, methyl methacrylate, allyl amine, vinyl alcohol, maleic anhydride, maleimide, carboxylate, vinyl carbamate, allyl sulfate, vinyl thiosulfate, vinyl sulfonate, allyl phosphate, vinyl phosphonate, vinyl alcohol, vinyl trimethylammonium chloride, other ethylenically unsaturated monomers substituted with ionic groups or precursors thereof, and the like. A second monomer includes a hydrophobic substituent, for example, styrene, C8–C30 α-olefin, acrylic acid-n-dodecyl ester, vinyl naphthalene, vinyl anthracene, (para n-dodecyl)styrene, other ethylenically unsaturated monomers substituted with hydrophobic groups, and the like.

A particularly preferred polymer is a maleic anhydride-α-olefin copolymer, for example, poly(maleic acid-alt-α-olefin, C24–C28) (PMA-OL), poly(maleic anhydride-alt-1-tetradecene) (PMA-TD), poly(maleic anhydride-alt-1-octadecene) (PMA-OD), and the like.

Other alternatives for the the immobilizing polymer can be any polymer that includes the functional substituents described above, i.e., at least an ionic group, or precursor thereof, and a hydrophobic group. Such polymers include appropriately substituted polyvinylalcohol, polyethers, polyacrylic acids, polyalkylacrylates, polymethacrylic acids, polyalkylmethacrylates, polystyrene, polystyrene sulfonates, polyvinylnaphthalene, polyethylvinylbenzene, polyaminostyrene, polyvinylbiphenyl, polyvinylanisole, polyvinylimidazolyl, polyvinylpyridinyl, polydimethylaminomethylstyrene, polyvinylamine, poly-N-alkylvinylamine, polyallylamine, poly-N-alkylallylamine, polydiallylamine, poly-N-alkyldiallylamine, polyalkylenimine, other polyamines, polyamides, polyacrylamides, polymethacrylamides, poly-N-alkylacrylamides, poly-N-alkylmethacrylamides, polydiallylmethylammonium chloride, polytrimethylammonium ethyl methacrylate, polytrimethylammonium ethyl acrylate, and copolymers thereof.

The molecular weight of the immobilizing polymer itself, i.e., prior to reaction with a biocatalyst or attachment to a biochip, should be large enough that there are significant interpolymer hydrophobic interactions between hydrophobic groups to allow the immobilizing polymer to stably coat the flow surfaces, yet small enough so that the polymer can be dissolved in a suitable solvent for coating. This is highly polymer dependent, e.g., polyacrylate can be much higher molecular weight than polystyrene sulfonate. The number average molecular weight of the polymer can be, for example, between about 2,000 and about 50,000, alternatively between about 2,500 and about 25,000, more preferably between about 5,000 and about 20,000, and most preferably between about 7,500 and about 15,000. A suitable solvent includes any solvent that can dissolve the immobilizing polymer, for example, protic solvents such as water, and alcohols; aprotic polar solvents such as N,N-dimethyl formamide, dimethyl sulfoxide, nitromethane; halogenated solvents such as chloroform, carbon tetrachloride, and trichloroethylene; ethereal solvents such as tetrahydrofuran; aryl solvents such as benzene, toluene, and xylenes; and the like. Suitable solvents can be made acidic or basic, for example, a polymer with carboxyl substituents can be more soluble in a basic alcohol.

The immobilizing polymer itself can be further, or alternatively, characterized by the numerical ratio of ionic groups, or precursors thereof, to hydrophobic groups. In this characterization, ionic groups, or precursors thereof, are counted by the number of charges that can be generated, e.g., a carboxylate and a carboxylic acid are each counted as one, and a maleic anhydride and a phosphate are each counted as two. Each hydrophobic group counts as one. In this fashion, the ratio of ionic groups to hydrophobic groups in the immobilizing polymer itself can be between about 1:20 to about 20:1, alternatively from about 1:8 to about 8:1, more preferably between about 1:5 to about 5:1, even more preferably between about 1:2 to about 2:1, or alternatively about 1:1. In a particularly preferred embodiment, the ratio of ionic groups to hydrophobic groups in the immobilizing polymer itself is about 2:1.

Alternatively, the polymer can be characterized by the molar ratio of monomers, separated into ionic monomers, i.e., those contributing an ionic group (or precursor thereof) and hydrophobic monomers, i.e., those contributing a hydrophobic group. The ratio between ionic and hydrophobic monomers can be between about 1:20 to about 20:1, alternatively from about 1:8 to about 8:1, more preferably between about 1:5 to about 5:1, even more preferably between about 1:2 to about 2:1, or most preferably about 1:1. In a particularly preferred embodiment, the ratio of ionic monomers to hydrophobic monomers is about 1:1.

The polymer can be produced in situ, or can be produced in whole or in part and then coated and adhered to the solid substrate. For example, maleic anhydride and an α-olefin can be polymerized using a radical initiator in the presence of the amine-functionalized biochip of structure A. The biomolecules can then be reacted with the immobilized polymer under suitable reaction conditions. Alternatively, the polymer can be produced separately (e.g., polymerizing maleic anhydride and an α-olefin) added to the amine-functionalized biochip, thereby immobilizing the polymer and coating the flow surface. Subsequently, the biomolecule can be added under suitable reaction conditions, thereby immobilizing the biomolecule. Alternatively, the polymer can be produced, the biomolecule can be immobilized thereon, and the biomolecule-polymer product reacted with the amine-functionalized biochip.

As used herein, a biomolecule is any biologically derived molecule that has biological activity, for example, binding activity, catalytic activity, and the like. A biomolecule is derived from any appropriate source, such as an enzyme domain extracted from a natural organism, a protein genetically engineered to be expressed in a different organism, a naturally derived peptide synthesized to contain an unnatural amino acid, and the like. A biomolecule can be a protein, a peptide, an antibody, an enzyme, an enzyme cofactor, a catalytic antibody, an oligonucleotide such as ribonucleic acid or deoxyribonucleic acid, a lipid, an oligosaccharide, a polysaccharide, a purified cell component, and the like. A biocatalyst is a biomolecule that can catalyze a chemical or biochemical reaction, and includes any associated cofactors necessary to carry out a particular catalytic transformation. A biocatalyst can include, for example, a catalytically functional portion of a catalytic antibody, an enzyme, an enzyme domain, a catalytic peptide, an oligonucleotide enzyme such as a ribonucleic acid enzyme or a deoxyribonucleic acid enzyme, and the like. Alternatively, the biocatalyst can be a catalytic antibody, an enzyme, or an enzyme domain. More preferably, the biocatalyst is an enzyme, most preferably, a catalytically functional portion of an oxidoreductase, a transferase, a hydrolase, a lyase, an isomerase, or a ligase, i.e., IUBMB (International Union of Biochemistry and Molecular Biology, www.chem.qmul.ac.uk/iubmb/ systematic enzyme classification (EC) numbers 1, 2, 3, 4, 5, and 6, respectively).

Figure 5A:
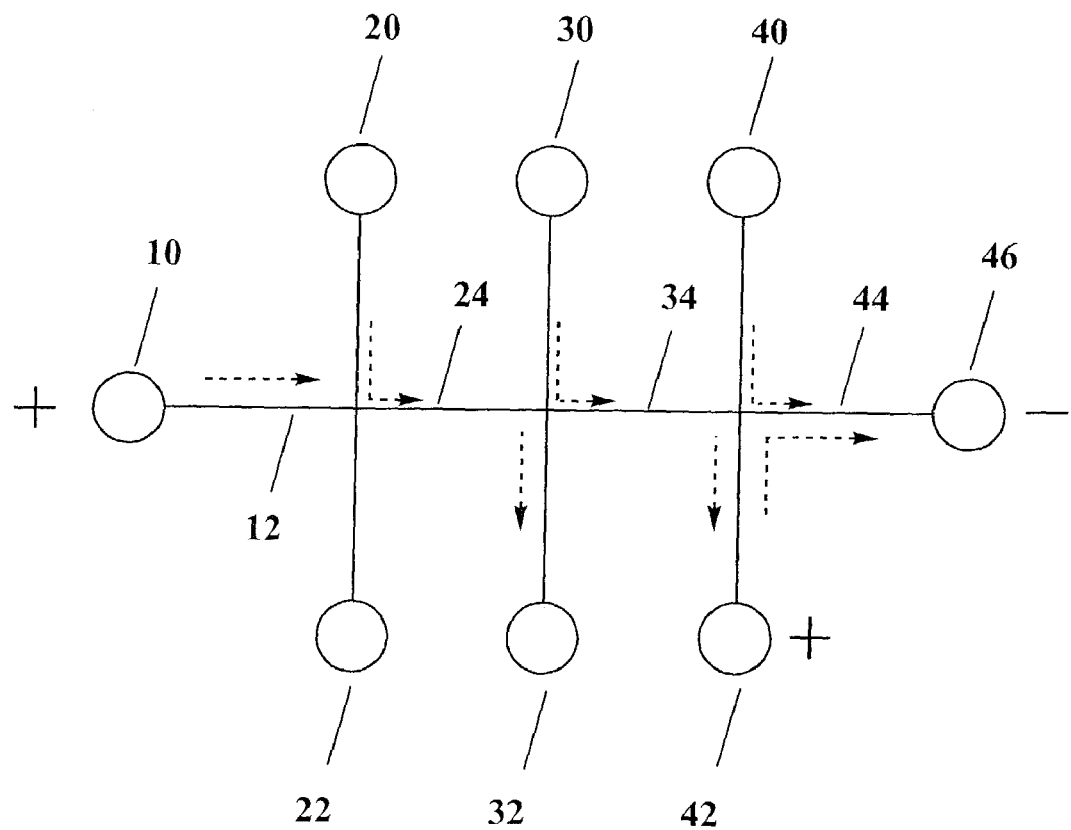
FIG. 5A depicts the 3-step multi-enzyme pathway incorporated into a PDMS (polydimethyl siloxane) biochip, wherein the three PMA-OD (poly(maleic anhydride)-co-1-octadecene) immobilized enzymes are spatially separated.

In one embodiment, a biomolecule is directed from a source on the biochip to a biomolecule-immobilizing group under suitable reaction conditions, thereby immobilizing the biomolecule to the immobilizing polymer at a flow surface. For example, FIG. 5A shows a schematic of a biochip where an enzyme, invertase, is directed from reservoir 20 to a flow surface coated with immobilizing polymer (PMA-OD), i.e., region 24, where the invertase is immobilized.

In another embodiment, at least two chemically distinct biomolecules are immobilized on a polymer at a flow surface. The chemically distinct biomolecules can be immobilized in the same location or in distinct locations. Alternatively, at least two chemically distinct biomolecules are separately directed and immobilized on polymers at spatially distinct flow surfaces, whereby the biomolecules are catalytically and spatially distinct. For example, FIG. 5A shows a schematic of a biochip where two catalytically distinct enzymes, invertase and glucose oxidase, are directed separately from reservoirs 20 and 30, respectively, and immobilized separately at locations 24 and 34.

As used herein, "chemically distinct" means biomolecules that differ in chemical structure, molecular formula, molecular weight, isotopic composition, cofactors, sequence (of monomers, amino acids, DNA base pairs, RNA base pairs, and the like), function, i.e., catalysis or binding, oxidation state, secondary structure, tertiary structure, and the like. "Catalytically distinct" or "distinct biocatalysts" means that two catalysts are capable of catalyzing different chemical or biochemical reactions.

The biomolecule immobilized on the polymer at the flow surface can be characterized relative to the amount of biomolecule theoretically needed to form a monolayer on the flow surface. It is believed that interpolymer hydrophobic interactions form a highly porous, three dimensional matrix at the flow surface, allowing immobilization of more biomolecules than needed for a monolayer. Thus, in one embodiment, the amount of biomolecule immobilized on the polymer at each flow surface is between about 100% and about 800% of a theoretical monolayer, alternatively between about 110% and about 500% of a theoretical monolayer, more preferably between about 125% and about 500% of a theoretical monolayer, and most preferably between about 150% and about 300% of a theoretical monolayer. Of course, in many embodiments, much less biomolecule will be required.

The biochip with an immobilized biomolecule can be used to conduct chemical or biochemical reactions, for example, catalysis, binding, polymerization, molecular recognition, and the like. For example, in one embodiment, a reactant is directed from a source to an immobilized biocatalyst under suitable reaction conditions, thereby producing a first reaction product. In another embodiment, the first reaction product is reacted with a second catalytically distinct immobilized enzyme, thereby producing a second reaction product. Alternatively, the first reaction product is directed to a second catalytically distinct biocatalyst that is immobilized at a spatially distinct flow surface, thereby producing a second reaction product in a sequential manner.

One particularly preferred embodiment of the invention is a microfluidics biochip, comprising at least one microfluidic reservoir and a plurality of microfluidic channels. The channels are each less than about 0.1 mm² in cross-sectional area, and the channels each comprise a flow surface. Furthermore, the channels are in microfluidic communication with each other and with the reservoir, and each channel is in microfluidic communication with at least two electrodes, whereby an electroosmotic flow can be generated at the flow surfaces. A polymer is coated on at least one flow surface, wherein the polymer is substantially adhered to the surface. The polymer comprises one or more ionic substituents of the same polarity selected from optionally substituted carboxylate, carbamate, sulfate, thiosulfate, sulfonate, phosphate, phosphonate, or hydroxyl. The polymer also includes one or more hydrophobic substituents selected from optionally substituted C8–C30 alkyl, a polycyclic alkyl, or a polycyclic aryl. The polymer also includes at least two catalytically distinct biocatalysts that are each immobilized to the polymer through an amide bond. The electrodes can be used to generate an electroosmotic flow to direct a reactant solution from the reservoir to a first catalytically distinct biocatalyst, whereby a first reaction product can be produced; and the first product from the first biocatalyst can be contacted with a to a second catalytically distinct biocatalyst, whereby a second reaction product can be produced.

As used herein, "suitable reaction conditions" include appropriate values for temperature, pressure, reaction time, pH, solvent, presence of biocatalyst cofactors, consumable reagents required such as adenosine triphosphate (ATP) or nicotinamide adenine dinucleotide phosphate (NADPH), and the like, that permit biological or biocatalytic activity.

EXEMPLIFICATION

Several microfluidic biochips were constructed by etching microfluidic channels into glass microscope slides or by molding channels into polydimethyl siloxane slabs. Slides were prepared as EOF controls (i.e., plain glass microchannels treated to activate siloxide anions on the channel surfaces), as immobilization controls (i.e., siloxide-activated channels functionalized with aminopropyl triethoxysilane (APTES) and then with glutaraldehyde), and as a test system to demonstrate the invention (i.e., siloxide-activated channels functionalized with APTES and PMA-OL, and PDMS (polydimethyl siloxane) channels coated with PMA-OD). The enzymes that were immobilized included soybean peroxidase (SBP), lipase, invertase, and glucose oxidase.

In these experiments, the ionic groups necessary to support the electroosmotic flow in the PMA-OL and PMA-OD coated biochips are provided by carboxyl groups. These groups are freed from the maleic anhydride groups in the PMA polymer when the maleic anhydride group reacts with either the enzyme, or, in the case fo the APTES-functionalized glass biochips, when the anhydride reacts tith the surface amine groups. The resulting negative charges ensured significant flow in the enzyme-bound microchannels.

Example 1

PMA-OL Coating Enhances EOF Versus Glutaraldehyde Control Chips

In FIG. 1, the flow rate as a function of EOF voltage applied to the biochip is shown for the EOF control (solid circle), the glutaraldehyde-control (solid triangle), and PMA-OL-coated channels (open circle). A linear relationship was obtained for all three cases. For 5% PMA-OL coated glass at 1500 V, a flow rate of about 100 nL/min (aqueous buffer containing 20% (v/v) DMF) was obtained. Under the same conditions, the flow rate for the 5% glutaraldehyde-control was only 10 nL/min. Such low flow rates are most likely due to the loss of negative charges on the microchannel walls, thereby slowing EOF-driven flow. By comparison, the EOF control (solid circle) is about 200 nL/min under the same conditions. Thus, the addition of negative charges by the free carboxylates in the PMA-OL provide a substantial fraction of the flow rate of the EOF control chip.

Example 2

PMA-OL Immobilized Enzyme Retains High Biological Activity

A single step reaction consisting of SBP catalyzed oxidation of p-cresol was examined:

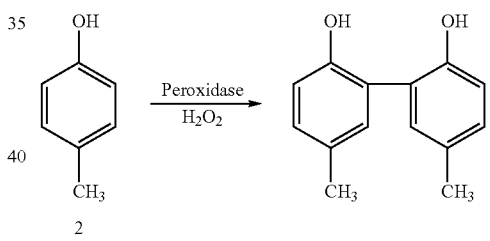

2

The reactions were conducted by SBP catalyzed reaction of cresol and $H_2O_2$ using a 2% PMA-OL-coated chip with 0.4 μg immobilized SBP, 20 mM p-cresol and 0.125 mM $H_2O_2$ in phosphate buffer containing 20% (v/v) DMF. Initially, the microchannel, with immobilized SBP, and product reservoir were filled with the DMF-buffer solution, and substrates were added to both substrate reservoirs. Substrates were supplied to the microchannel by EOF allowing product accumulation to take place.

Figure 2A:
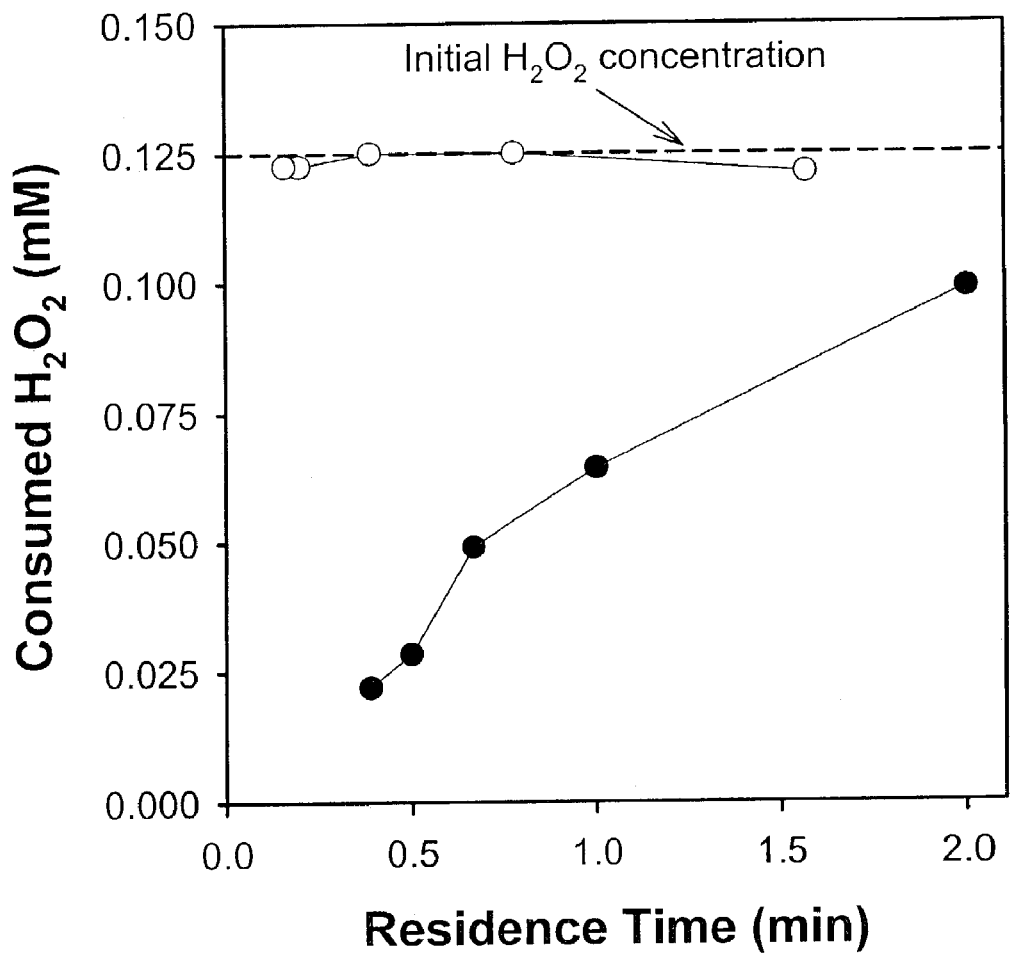
FIG. 2A graphs high retained biological activity of PMA-OL immobilized soybean peroxidase (SBP) as shown by $H_2O_2$ consumption by on the biochip in 2% loading (filled circles) and 10% loading (open circles).
Figure 2B:
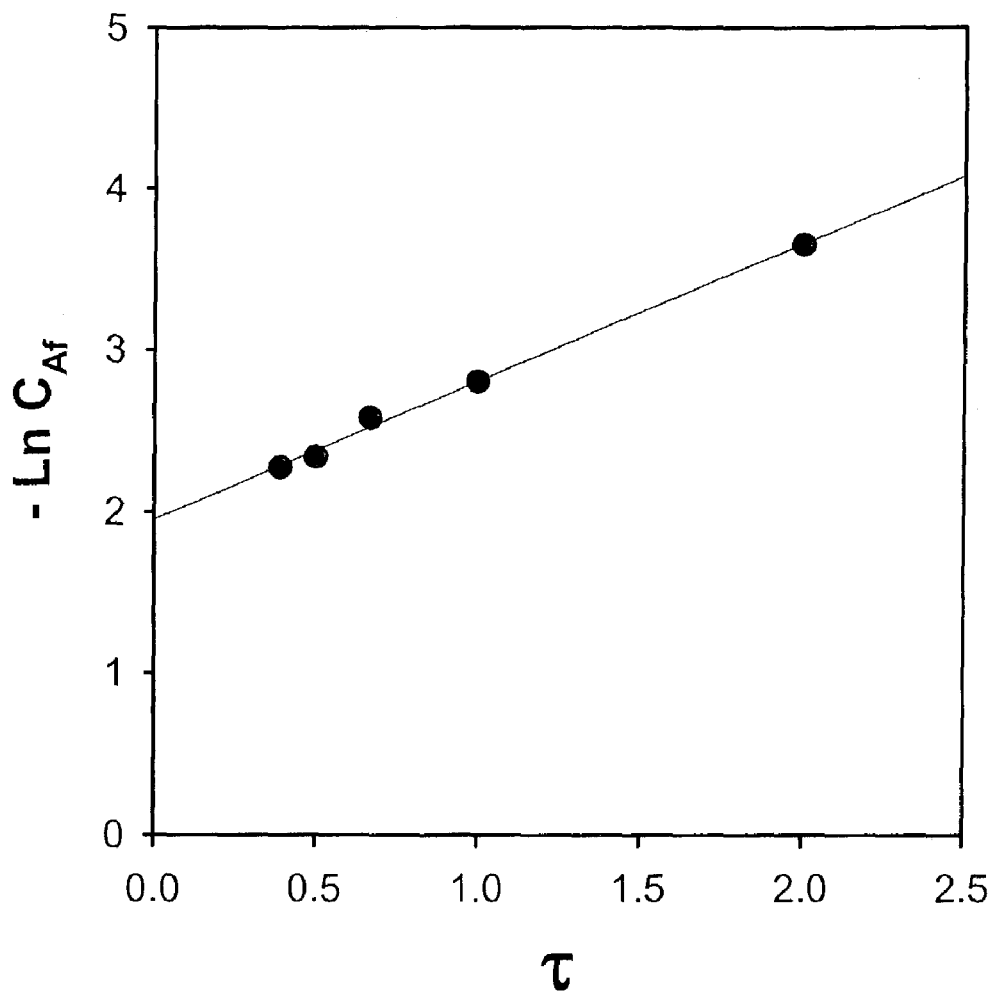
FIG. 2B graphs the kinetics of PMA-OL-immobilized soybean peroxidase.

As shown in FIG. 2A, SBP was active on the PMA-coated microchannel using either 2% (filled circles) or 10% (open circles) (w/v) PMA loading, corresponding to 0.4 and 0.6 μg SBP loaded, respectively. For the higher enzyme loading, complete consumption of $H_2O_2$ was achieved at residence times as short as 0.2 min. Hence, SBP retained high activity in the biochip, and the rate of reaction was limited by the rate of delivery of $H_2O_2$ to the microchannel. For the lower amount of SBP loaded into the microchannel, the enzyme became rate limiting, with up to ca. 80% conversion for a 2 min residence time. This enabled evaluation of the reaction kinetics of the immobilized SBP, which followed a plug flow Michaelis-Menten rate model (FIG. 2B), based on Equation 2:

$$-\left(\ln C_{Af} + \frac{C_{Af}}{K_m}\right) = \left(\frac{V_{\max}}{K_m}\right)\tau - \left(\frac{C_{Ao}}{K_m} + \ln C_{Ao}\right) \quad (2)$$

In this equation, $C_{Af}$ is the residual $H_2O_2$ concentration in the microchannel, T is residence time of substrate in the microchannel, and $C_{Ao}$ is initial $H_2O_2$ concentration (0.125 mM). The term $C_{Af}/V_{\max}$ was assumed to be small relative to the other term on the left-hand side of Eq. 4 and was, therefore, ignored to simplify the expression. This expression can be used when the limiting substrate (e.g., $H_2O_2$) conversion is high at long residence times, and the plot in FIG. 2B allows calculation of the $V_{\max}/K_m$ (slope) and a Y-intercept that provides a value for $K_m$.

Calculation of SBP's kinetics of p-cresol oxidation reveals that the kinetics are, surprisingly, largely unaffected by immobilization to PMA in the 90 nL microchannels. Specifically, the $K_m$ of SBP in the biochip was 0.98±0.12 mM, compared with 0.95±0.14 mM for p-cresol oxidation in soluble forms in both 5-mL volumes (in 20 mL scintillation vials) and 20 μL volumes in 384-well plates. Similarly, the $V_{\max}$ was 0.21±0.03 μmol $H_2O_2$ converted/mg SBP-min, which was essentially identical (0.20±0.03 μmol $H_2O_2$ converted/mg SBP-min) for the soluble enzyme at larger scales[12]. These results indicate that SBP displays intrinsically native activity even in the immobilized form at the microscale, and further attests to the mild immobilization conditions afforded by a polymer containing ionic and hydrophobic groups such as PMA-OL. Moreover, the PMA-OL matrix appeared to be highly porous, as the enzyme is immobilized at a higher concentration than would be expected in a single monolayer, yet no diffusional limitations are apparent, as the immobilized SBP in the microchannel has a $V_{\max}$ identical to that in solution.

Example 3

PMA-OL Biochip Immobilizes Two Distinct Enzymes with High Activity

A coupled lipase/peroxidase biochip was prepared where the enzymes were co-immobilized using 5% (w/v) PMA solution. Lipase B from *C. antarctica* was used for the first reaction, the hydrolysis of p-tolyl acetate, which yields acetic acid and p-cresol, followed by coupling of the cresol to poly(p-cresol) using SBP and $H_2O_2$:

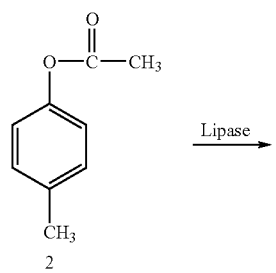

-continued

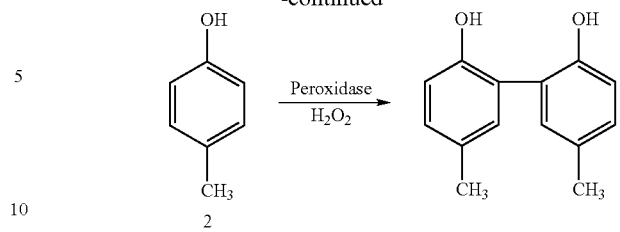

The lipase was used at a 10-fold higher concentration than SBP because of the expected low reactivity of the lipase on the cresol ester, which was not expected to be a highly reactive substrate of the enzyme. Reactions were initiated upon flowing solutions of 15 mM p-tolyl acetate and 0.25 mM $H_2O_2$ in phosphate buffer (pH 7.0) containing 20% (v/v) DMF. The solubility of the tolyl acetate was greatly facilitated by the presence of DMF. Reactions were performed in the microchannel with 0.6 μg total enzyme, 15 mM p-tolyl acetate, 0.25 mM $H_2O_2$ and in the 384-well plate with 100 μg/mL lipase, 10 μg/mL SBP, 15 mM p-tolyl acetate, and 0.25 mM $H_2O_2$ in phosphate buffer containing 20% (v/v) DMF.

Figure 3:
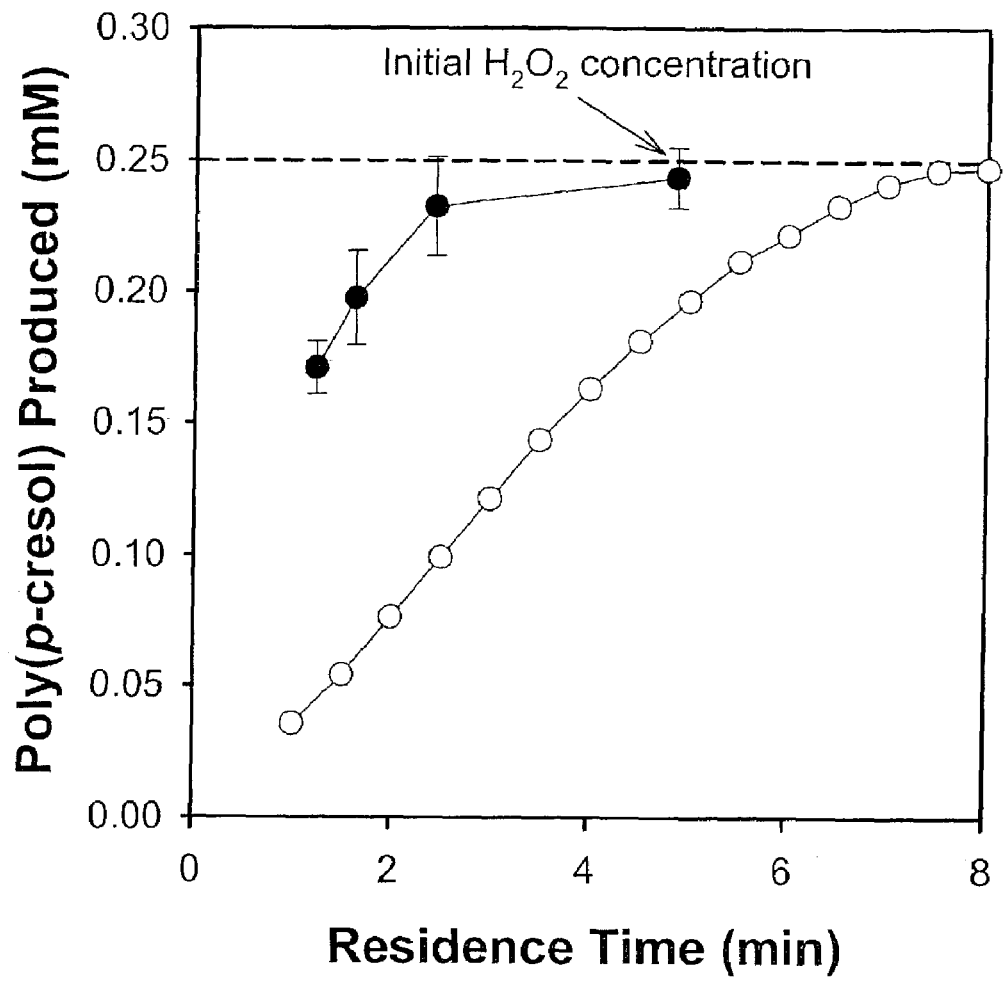
FIG. 3 graphs the high catalytic activity of two PMA-OL immobilized enzymes for poly(p-cresol) production on the biochip (filled circles) compared to a solution control (open circles).

The two-step enzymatic transformation was sufficiently reactive to give complete conversion of the $H_2O_2$ supplied with a residence time of 3 min FIG. 3 (filled circles). The $K_m$ and $V_{\max}$ values for lipase in the microchannel were calculated to be 0.59 mM and 0.13 μmol/mg lipase-min. Also shown in FIG. 3 is the reactivity of the two-step enzyme transformation in solution in a 384-well plate using 100 μg/mL lipase and 10 μg/mL SBP (open circles). In this case, consumption of $H_2O_2$ was followed as a function of reaction time. Clearly the high loading of lipase in the microchannel and its high activity coupled with the high activity of SBP resulted in an efficient bienzymic system.

The higher reactivity of the bienzymic system in the microfluidic biochip is likely due to the higher concentration of the rate limiting enzyme, in this case the lipase, in the biochip than in free solution. Assuming 0.6 μg total protein loading (the lipase and SBP are of similar size), then ca. 0.55 μg of lipase was immobilized to the microchannel, giving ca. 5.5 mg/mL lipase concentration. This is far higher than the 100 μg/mL lipase, even if the aforementioned calculation was an overestimate (we did not determine the loading density of lipase in the microchannel) used in free solution in 384-well plates.

Example 4

PMA-OL Biochip Immobilizes Three Distinct Enzymes with High Activity

In Example 4, a three-enzyme biochip was constructed to demonstrate a 3 step reaction sequence that is purely synthetic, i.e., is a non-natural pathway. Invertase cleaves sucrose into glucose and fructose:

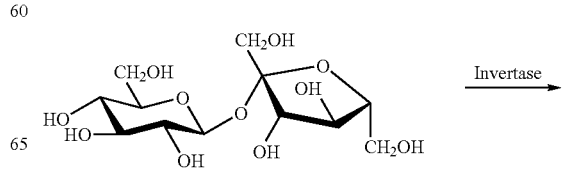

-continued

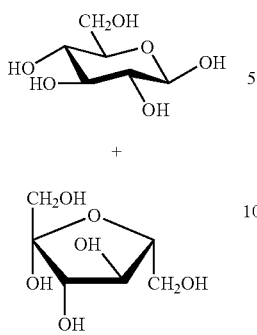

glucose oxidase oxidizes glucose using $O_2$ to produce $H_2O_2$;

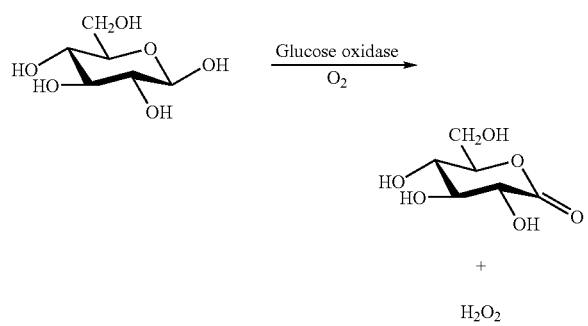

and SBP uses the $H_2O_2$ to produce poly(p-cresol):

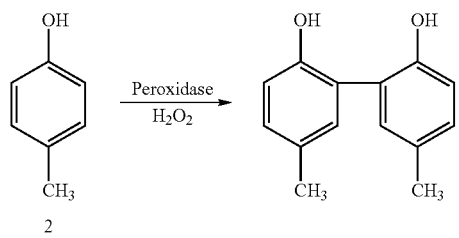

The immobilized and solution phase systems used the three enzymes, invertase, glucose oxidase, and SBP in a ratio of 10:10:2. Reactions were performed in the microchannel with 0.6 µg total enzyme, 1 mM sucrose, and 20 mM p-cresol and in solution with 100 µg/mL invertase, 100 µg/mL glucose oxidase, 20 µg/mL SBP, 1 mM sucrose, and 20 mM p-cresol in phosphate buffer containing 20% (v/v) DMF.

Figure 4:
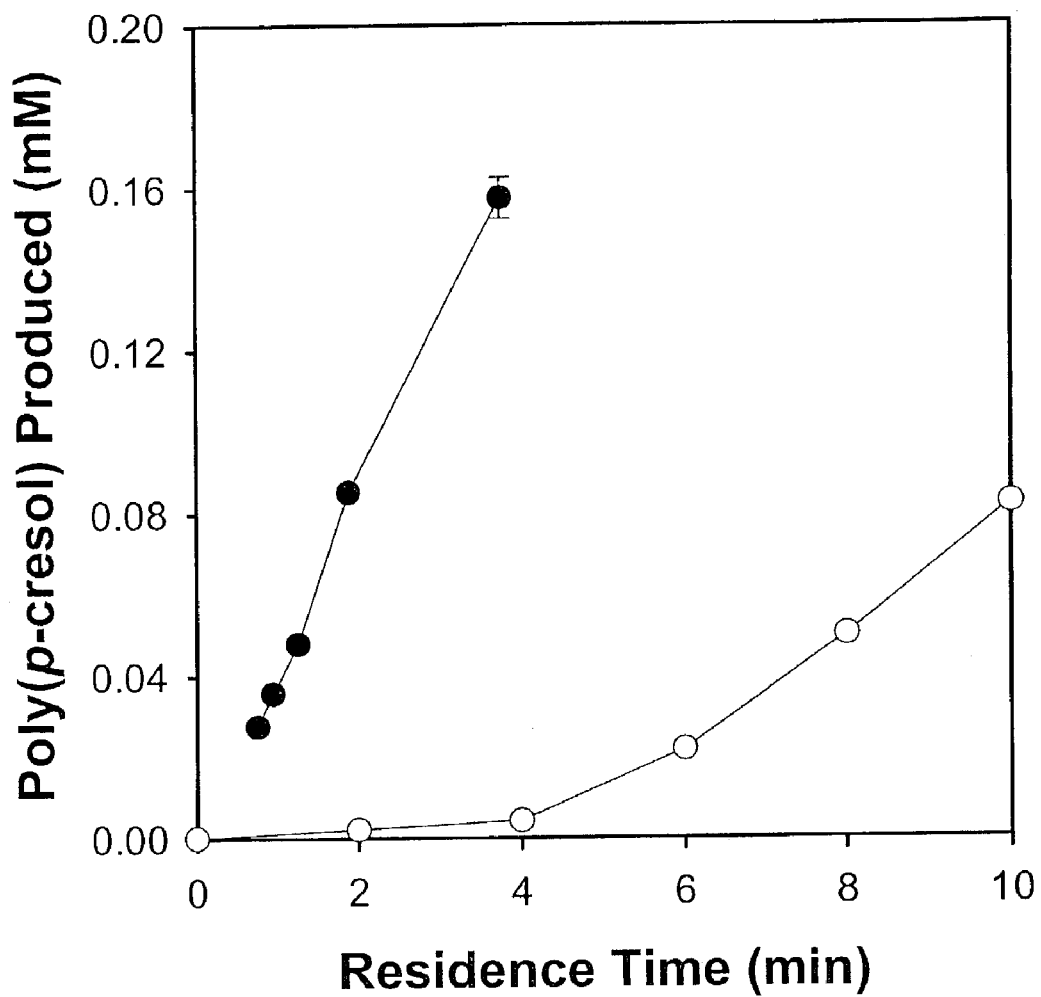
FIG. 4 graphs the high catalytic activity of three PMA-OL immobilized enzymes for poly(p-cresol) production on the biochip (filled circles) compared to a solution control (open circles).

FIG. 4 shows a comparison of the biochip reaction (filled circles) with that of a solution-phase reaction in the 384-well plate (open circles), also performed in the presence of 20% (v/v) DMF. As with Example 3 above, the microchannel reaction was much better than the solution-phase reaction, again likely because of the higher concentrations of the invertase and glucose oxidase in the biochip than in free solution. Interestingly, the microchannel reactions did not show a lag in product formed in the trienzymic pathway. This is likely due to the higher concentration of the rate limiting enzyme (invertase or glucose oxidase) in the microchannel as compared to free solution, thereby resulting in faster formation of $H_2O_2$ to feed the SBP reaction leading to poly(p-cresol).

Example 5

Biochip Conducts Multiple Sequential Catalyzed Reactions

In Example 5, the three-enzyme system of Example 4 was established on a PDMS biochip, wherein the three enzymes were immobilized at distinct locations. FIG. 5A shows a schematic of the PDMS biochip. The substrate sucrose is provided from reservoir 10 and is directed down channel 12 towards the product reservoir 46. At region 24, the sucrose is cleaved by immobilized invertase into glucose and fructose. At region 34, the glucose reacts with immobilized glucose oxidase to release $H_2O_2$. The p-cresol substrate is directed from reservoir 42 to region 44, where immobilized SBP reacts the p-cresol and $H_2O_2$ from the previous step to produce poly(p-cresol). The poly(p-cresol) product is then directed to reservoir 46.

Figure 5B:
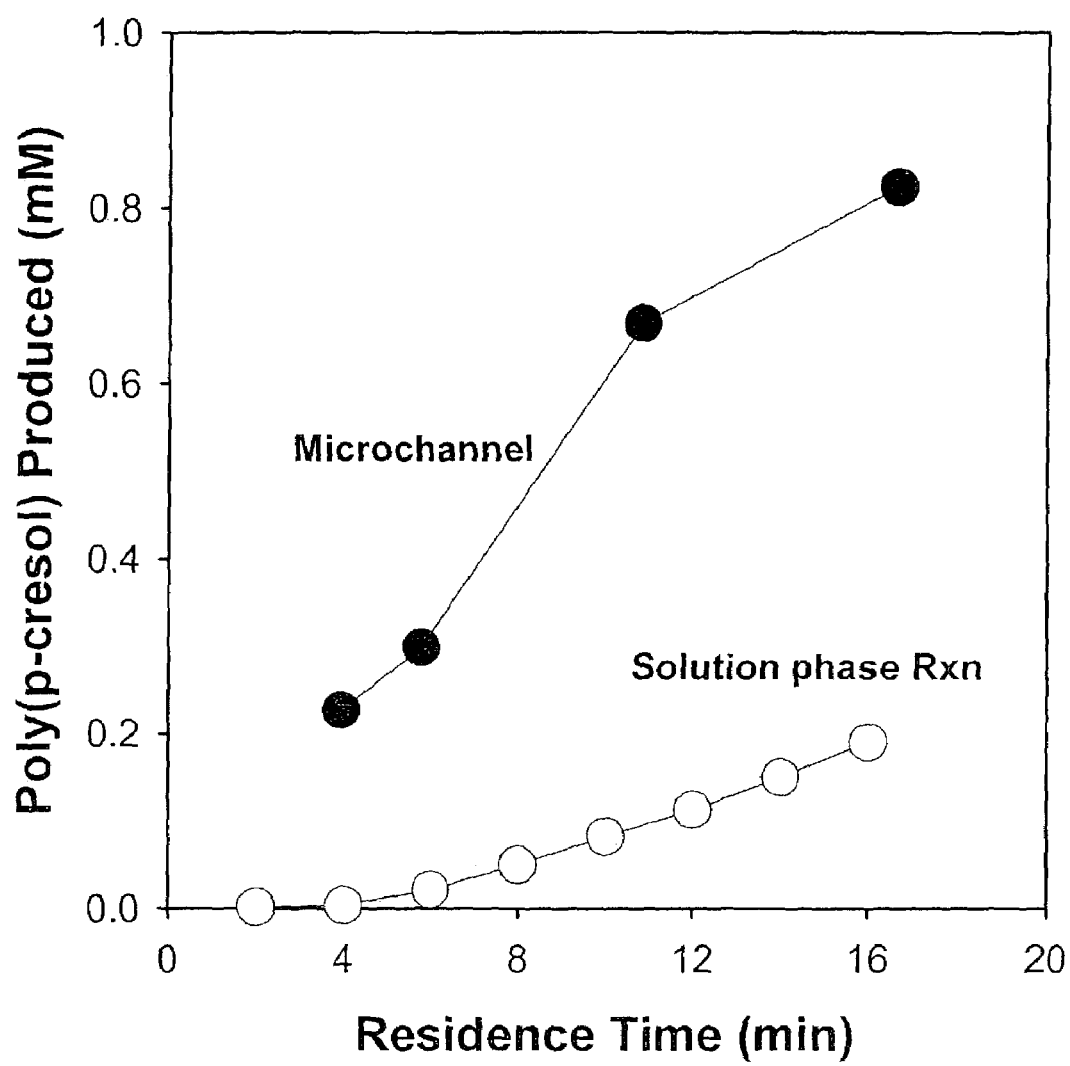

FIG. 5B shows a comparison of the biochip reaction (filled circles) with that of a solution-phase reaction in the 384-well plate (open circles), also performed in the presence of 20% (v/v) DMF. As with the preceding examples, the microchannel reaction was much better than the solution-phase reaction, again likely because of the higher enzyme concentrations in the biochip than in free solution. Here, the overall microchannel reaction is slower than in Example 4, principally because the reaction sequence has been spatially, and therefore temporally separated. However, the microchannel reaction is still considerably faster than the solution reaction.

As in Example 4, the immobilized and solution phase systems used the three enzymes, invertase, glucose oxidase, and SBP in a ratio of 10:10:2. Reactions were performed in the microchannel with 0.6 µg total enzyme, 1 mM sucrose, and 20 mM p-cresol and in solution with 100 µg/mL invertase, 100 µg/mL glucose oxidase, 20 µg/mL SBP, 1 mM sucrose, and 20 mM p-cresol in phosphate buffer containing 20% (v/v) DMF.

Materials

SBP (54 purpurogallin units/mg solid; RZ=1.3), fluorescein isothiocyanate (FITC)-labeled horseradish peroxidase (HRP), invertase from *Saccharomyces cerevisiae* and glucose oxidase from *Aspergillus niger* were purchased from Sigma (St. Louis, Mo.). Lipase B from *Candida antarctica* (Chirazyme L-2) was purchased from BioCatalytics (Pasadena, Calif.). 3-Aminopropyltriethoxysilane (APTES), poly (maleic anhydride-alt-α-olefin) (PMA-OL), glutaraldehyde, p-cresol, tolyl acetate, toluene, methanol (MeOH) and dimethylformamide (DMF) were purchased from Aldrich (Milwaukee, Wis.). Hydrogen peroxide ($H_2O_2$), $NH_4OH$, NaOH, and borosilicate glass microscope slides were obtained from Fisher Scientific (Pittsburgh, Pa.). Buffered oxide etch was purchased from Doe and Ingalls, Inc (Boston, Mass.). All other solvents and reagents were obtained commercially at the highest purity available and used without further purification.

Unless otherwise specified, substrates (20 mM p-cresol and 0.125 mM $H_2O_2$) were dissolved in 0.1 M sodium phosphate buffer (pH 7.0) containing 20% (v/v) DMF (to aid in p-cresol solubility). The substrates were loaded into opposite reservoirs on the upstream side of the T-channel; each with 80 µL of 40 mM p-cresol and 0.25 mM $H_2O_2$ in phosphate buffer containing 20% DMF. The product reservoir was initially filled with 40 μL of phosphate buffer containing 20% DMF. After initiating different flow rates by applying different voltages between the substrate (anode) and product (cathode) reservoirs for 1 h, 20 μL of sample was withdrawn from the product reservoir. Minimal electrolysis gases were observed to form at voltages less than 2500 V.

Glass Biochip Fabrication

Figure 6:
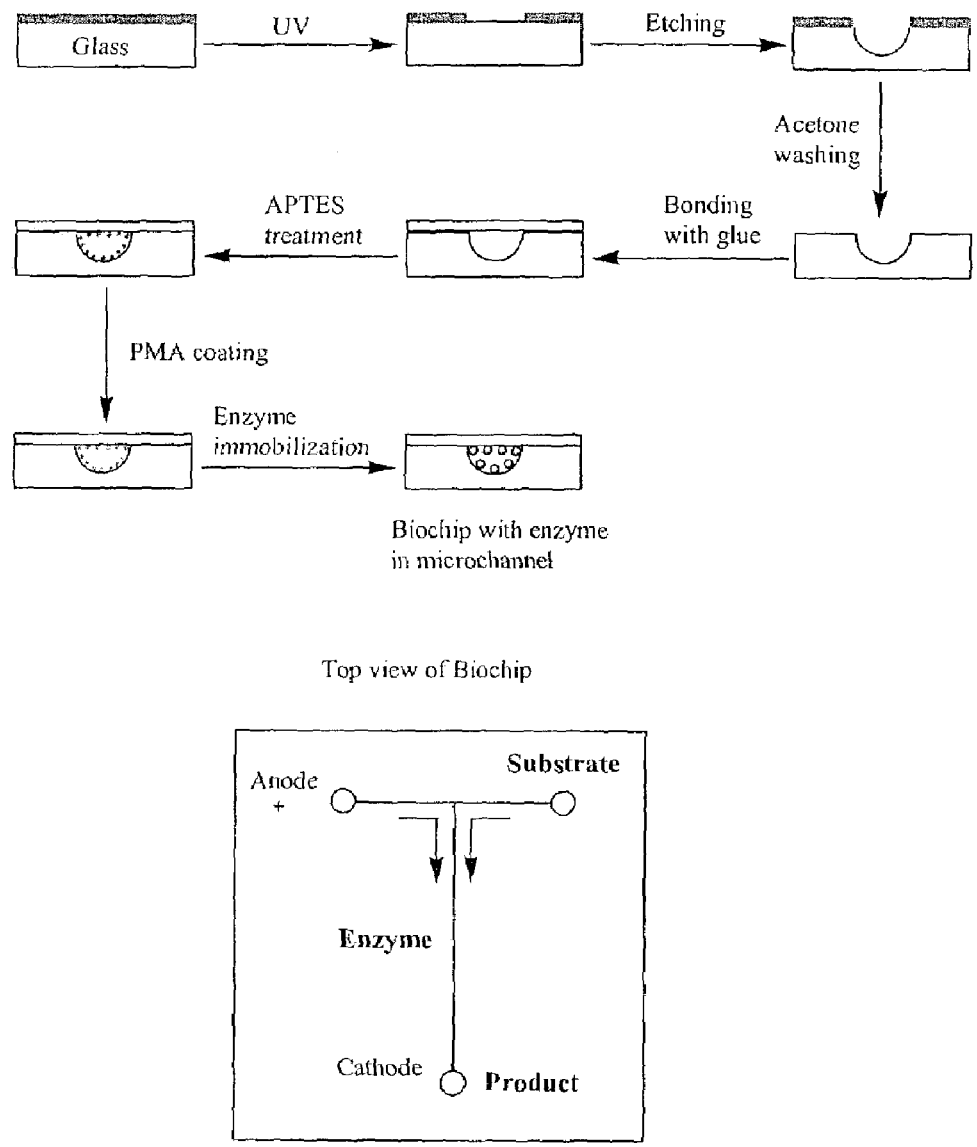
FIG. 6 depicts the steps in fabrication of microfluidic components on a glass slide for a biochip.

Borosilicate microscope slides were cleaned with isopropyl alcohol and acetone in a Class 100 clean room facility. The biochip consisted of a simple T-shaped microchannel with two substrate reservoirs and a product reservoir, and was fabricated using standard photolithographic techniques, shown schematically in FIG. 6. Briefly, the pattern from a photomask was transferred onto a glass slide, which was spin-coated with a layer of positive photoresist (Shipley 1813, Microlithography Chemical Co., Watertown, Mass.). Wet etching was performed using 10:1 buffered oxide etch solution for 45 min. The dimensions of the channel, as measured using a profilometer (Alpha-Step 2000, Tencor Instruments, Mountain View, Calif.), were 15 μm deep and 200 μm wide at the center. The microchannel was 30 mm long (V=90 nL) and each arm of the T channel was 10 mm long. Holes were drilled into the end of the channels to act as reservoirs for sample withdrawal and addition of substrate solutions. The drilling dust was removed in an ultrasonic bath before cover plate bonding.

The silanol groups on the surfaces of the etched glass slide and the cover plate were activated by treating with a 1:1 solution of $NH_4OH$ and $H_2O_2$ at 70° C. for 25 min. Channels activated in this manner could be used as the EOF control without further surface modification. After the glass slide and cover plate were rinsed with distilled water and dried using a nitrogen gun, bonding was performed using UV-cured glue, lens bond type SK-9 (Summers Optical, Fort Washington, Pa.). The glue was spread between the cover plate and the etched glass slide by capillary action and cured at room temperature by UV irradiation at 365 nm for 1 h. Subsequently, additional glass tubes of 100 μL volume as substrate and product reservoirs and platinum electrodes were attached to the drilled holes using 2-ton epoxy glue (ITW Devcon, Danvers, Mass.).

Surface Modification of Glass Biochip with PMA-OL and Glutaraldehyde

Figure 7A:
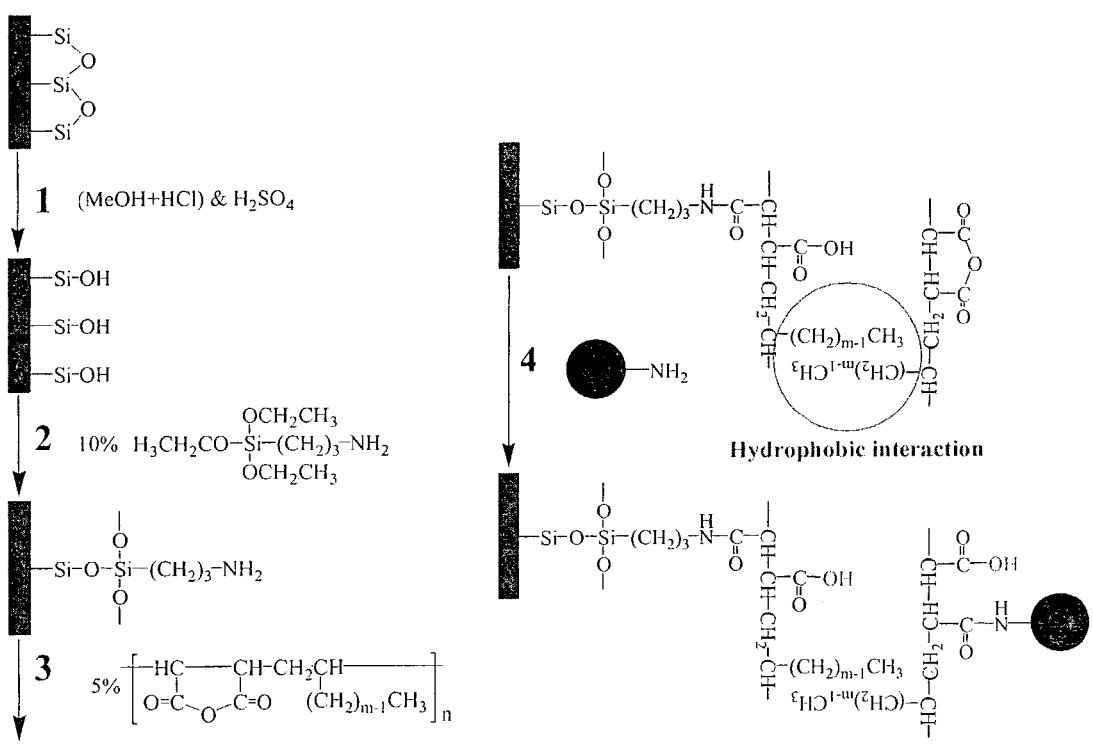
FIG. 7A depicts the chemistry of immobilizing an enzyme on a glass microfluidic surface using PMA-OL and APTES (aminopropyl triethoxysilane).
Figure 7B:
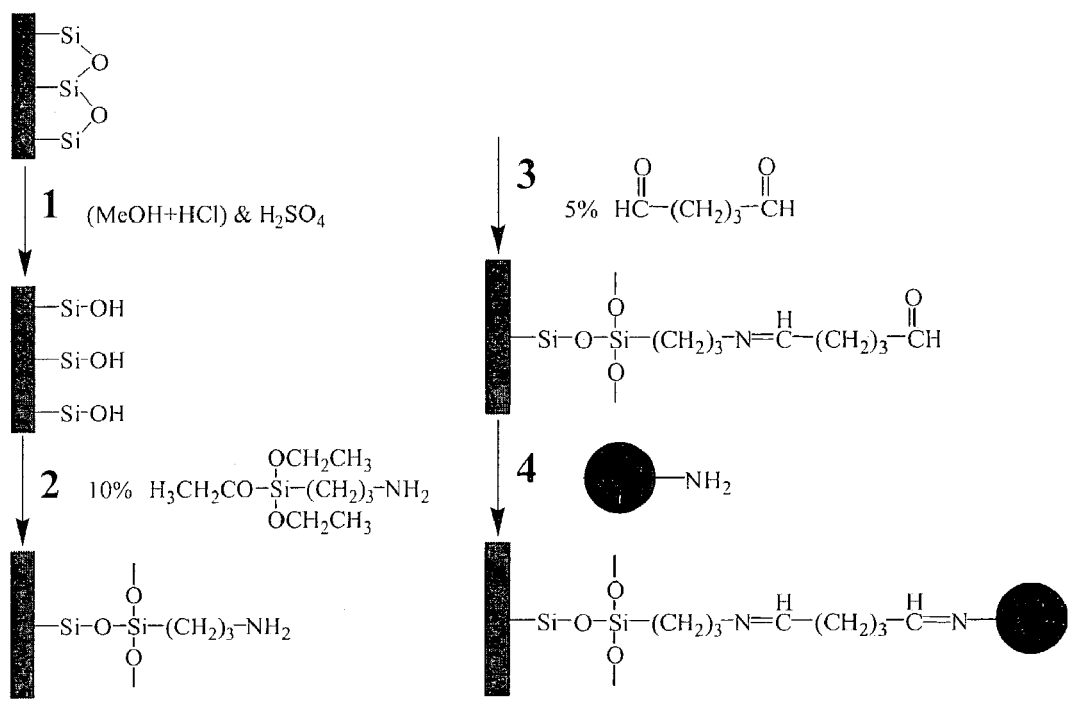
FIG. 7B depicts the chemistry of immobilizing an enzyme on a glass microfluidic surface using glutaraldehyde and APTES.

FIGS. 7A and 7B show schematically the steps involved in derivatizing the surface of the microchannels with PMA-OL and glutaraldehyde, respectively. The dark circle with the pendant —$NH_2$ group represents the enzyme. First, the internal surface of the microchannel was washed with MeOH:HCl (1:1) and then concentrated $H_2SO_4$ each for 5 min and removing the solutions by vacuum. MeOH:HCl and $H_2SO_4$ were loaded into substrate reservoirs (with a micropipette) with one outlet (product reservoir) connected to a vacuum pump (25 mm Hg) to enable flow into the microchannel. The microchannel was then rinsed with deionized distilled $H_2O$ for 30 min to give a solution pH of 7.0 and to provide silanol OH groups on the surface. Excess water in the microchannel was removed by washing with acetone and the biochip was dried at 110° C. for 3 h. Amino group functionalization was achieved by addition of 10% (w/v) of APTES in anhydrous toluene containing 0.5% (v/v) $CH_2Cl_2$, and 10 μL of this solution was supplied to the microchannel by vacuum. Concentrated APTES, therefore, was not exposed to air and humidity, and this prevented oxidation and hydrolysis. The biochip was dried at 90° C. for 2 h and then the microchannel was rinsed three times with toluene.

A thin PMA-OL coating was prepared on the microchannel using 5% (w/v) of PMA-OL in toluene, and supplying 4 μL of this solution by vacuum. After removing excess PMA-OL in the microchannel, the biochip was dried at 90° C. for 1 h. To wet the microchannel, a series of washings were performed with acetonitrile (ACN), ACN:$H_2O$ (1:1), and deionized distilled $H_2O$; each kept in the microchannel for 15 min and then removed by vacuum. Excess PMA-OL in the substrate and product reservoir was then removed by washing with toluene.

For glutaraldehyde modification, the microchannel was rinsed with toluene, ACN:$H_2O$ (1:1), and deionized distilled $H_2O$ three times following APTES treatment[8]. Glutaraldehyde (5%, v/v) in 0.1 M sodium phosphate buffer (pH 7.0) was loaded into the substrate reservoirs at room temperature and supplied to the biochip for 10 min by vacuum, and then for 2 h by EOF at 500 V. Excess glutaraldehyde was rinsed out of the microchannel by vacuum with 0.1 M sodium phosphate (pH 7.5) containing 1 mM $MgCl_2$ for 30 min. A high voltage power supply (Model 215, Bertan Associates, Inc., Syosset, N.Y.) was used to maintain a constant voltage difference for EOF between substrate reservoirs and product reservoir.

Enzyme Immobilization

Soybean peroxidase (SBP) (2 mg/mL) in 0.1 M sodium phosphate buffer (pH 7) was supplied to the PMA-coated or glutaraldehyde-derivatized microchannel for 8 h by EOF at 500 V to immobilize enzyme. All enzyme and substrate solutions were filtered prior to use to prevent particulates from clogging the microchannel. A hydrophilic syringe-driven filter unit with 0.45 μm pore size was used for the filtration (Millex-LCR, Millipore Co., Bedford, Mass.). The enzyme solution was replaced every 2 h due to the pH change in the reservoirs as a result of the electrolysis of water generating $H^+$ and $OH^-$ ions. Small bubbles that often formed in the microchannel were removed by vacuum. To remove excess enzyme after immobilization and before reaction, the microchannel was rinsed with phosphate buffer solution for 4 h by EOF at 1000 V. Immobilized FITC-labeled HRP was visualized in the microchannel using a Spot RT camera attached to a Nikon Eclipse TE 200 inverted microscope with TE-FM Epifluorescence attachment (Micro Video Instruments, Avon, Mass.).

PDMS Biochip Fabrication

A 1:1 mask was created by printing a high-resolution drawing of the desired microfluidic features as a negative (i.e., with the desired microfluidic features transparent) on a standard transparency film. A silicon master was created in a class-100 clean room facility from a silicon wafer (Silicon Quest International, Inc., Santa Clara, Calif.). The silicon wafers were cleaned with isopropyl alcohol and acetone, a layer of SU-8 negative photoresist (Microlithography Chemicals Co., MA) was spin-coated at 2000 rpm and 40 sec, and the coated wafer was pre-baked at 90° C. for 20 min. The coated wafer was aligned and exposed to ultraviolet light at 8.4 mW/$cm^2$ (365 mm) for 50 sec using a mask aligner through direct contact with the transparency film mask. After post baking the wafer for 5 min at 90° C., it was developed by immersion into SU-8 thinner solution (Microlithography Chemicals Co., MA) for 1 min followed by immersion into SU-8 developing solution (Microlithography Chemicals Co., MA) until unmodified photoresist was removed, about 15 min. The dimensions of the pattern on the silicon master were determined using a profilometer (Alpha-Step 2000, Tencor Insturments, Mountain View, Calif.).

A 10:1 weight ratio of monomer and curing agent (Sylgard 184, Dow Corning Co., MI) was mixed and degassed under vacuum. This mixture was poured over the silicon master and cured at 70° C. for 2 hours. The patterned PDMS substrate thus formed was peeled off, cut to working dimensions, and sealed using a cover slab of PDMS. This was achieved by oxidizing the common surfaces of the substrate and the cover slab using oxygen plasma for 10 sec and then bringing them into conformal contact.

PDMS Biochip Surface Polymer Coating and Enzyme Immobilization

A thin PMA-OD coating of the microchannels was obtained by flowing a 0.5% (w/v) of PMA-OD in acetone (4 μL) through the whole microfluidic network (FIG. 5A) using a vacuum. The enzymes (10 mg/mL Invertase (reservoir 20), 10 mg/mL Glucose oxidase (reservoir 30), and 2 mg/mL SBP (reservoir 40)) were supplied by electro-osmotic flow (250 V and 4 hrs) to spatially immobilize them in the microchannel at locations 24, 34, and 44, respectively. Excess enzyme was washed with phosphate buffer (pH 7.0) containing 20% DMF for 30 min. The three-step enzymatic reactions were carried out by supplying substrates 1 mM sucrose (from reservoir 10) and 20 mM p-cresol (from reservoir 42) for 1 hour.

Measurement of Enzyme Loading Density

To estimate the immobilized enzyme content in the microchannel, the amount of immobilized SBP on a glass surface at different PMA concentration was measured using the micro-BCA method (Pierce Biotechnology, Inc., Rockford, Ill.). Glass (1 cm×1 cm) was incubated for 16 h in 10 mg/mL SBP solution after coating with different concentrations of PMA and washed with phosphate buffer and distilled water for 4 h before BCA analysis. The glass squares with SBP covalently attached were incubated at 60° C. for 1 h in the micro-BCA working reagent (see www.piercenet.com). The chromogenic product of the micro-BCA assay is soluble in the assay reagent and was removed from the immobilized enzyme preparation for spectrophotometric measurements. The protein content was then determined based on a standard curve with SBP in solution.

Fluorescence and Flow Velocity Measurement

Spectrofluorophotometry was used to determine the activity of SBP. The intrinsic fluorescence of oligo- and polyphenols can be used to monitor the formation of product as the monomeric phenols have relatively minimal fluorescence. Sample analysis was performed in a 384-well plate (Simport Plastics, Quebec, Canada) and the reactions were monitored by measuring the relative fluorescence intensity (RFU) using a BioAssay Reader HTS 7000 Plus (Perkin Elmer, Norwalk, Conn.) at an excitation wavelength of 325 nm and emission wavelength of 405 nm.

To determine the flow rate of substrate in the microchannel at a particular voltage, a known concentration of the fluorescent p-cresol oligomeric product (original RFU of 8,500) was transported through the microchannel by EOF. The product reservoir was filled with 40 μL of phosphate buffer with 20% DMF. After 1 h of EOF operation, 20 μL samples were withdrawn from the product reservoir and the RFU measured. The flow rate was calculated by correlating the measured RFU as a function of the dilution ratio to known oligomeric concentration.

Calculation of Reaction Yield

SBP catalysis gives a diverse array of oligomers that appear to have widely different fluorescence properties. Moreover, fluorescence intensity does not scale linearly with concentration, as shown in Eq. 2, where where $\phi$ is the quantum efficiency, $I_0$ is the incident radiation power, $\epsilon$ is the molar absorptivity, b is the path length of the cell, and c is the molar concentration[16].

$$F = \phi I_0 (1 - e^{-\epsilon bc}) \quad (2)$$

Thus, the biochip operating at different flow rates, thereby resulting in different degrees of product dilution in the product reservoir, will give different fluorescence intensities even if the conversion is identical. To overcome this problem, we generated poly(p-cresol) in a 5 ml reaction containing 20 mM p-cresol, 0.125 mM $H_2O_2$, and 20 μg/ml SBP in phosphate buffer (pH 7.0) with 20% (v/v) DMF to obtain a product with a net relative fluorescence (RFU) of 8,500. This product was then diluted up to 100 fold and the fluorescence intensity measured as a function of dilution. As expected, the RFU was logarithmically dependent on dilution (curve not shown), and could be represented by the expression in Eq. 3, where X is the dilution ratio in the product reservoir and A is the original RFU of the sample after correcting for dilution.

$$\text{Log } Y = -0.85 \text{ Log } X + \text{Log } A \quad (3)$$

Based on this expression the dilution ratio (X) in the product reservoir at different voltages was calculated from the original RFU (8,500) in the substrate reservoir (A) and diluted RFU measured in the product reservoir (Y).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of immobilizing a biomolecule on a microfluidics biochip, comprising the steps of
    a) providing a microfluidic biochip, comprising
        a microfluidic component comprising a flow surface;
        at least two electrodes, whereby an electroosmotic flow can be generated at the flow surface;
        an immobilizing polymer that is substantially adhered to the flow surface, the polymer comprising a backbone to which are attached
            a first substituent selected from ionic groups of the same polarity and covalent precursors of the ionic groups, wherein the first substituent is optionally a biomolecule immobilizing group;
            a second substituent that is a hydrophobic group; and
            optionally a third substituent that is a biomolecule-immobilizing group;
            wherein the polymer comprises at least one substituent that is a biomolecule-immobilizing group;
    b) applying a motive force selected from pressure, electroosmotic force, capillary action, and centrifugal force, thereby generating flow;
    c) directing a biomolecule from a source to the polymer by employing the flow; and
    d) reacting the biomolecule with the biomolecule-immobilizing group under suitable reaction conditions, whereby the biomolecule is immobilized.
2. The method of claim 1, wherein the microfluidic component is a microchannel, wherein a cross-sectional area of the microchannel is less than about 0.1 $mm^2$.

3. The method of claim 2, wherein the biomolecule is a biocatalyst, comprising
a catalytically functional portion of an antibody, an enzyme, a peptide, or an oligonucleotide; and
optionally, a cofactor.

4. The method of claim 3, wherein the biocatalyst comprises
a catalytically functional portion of an oxidoreductase, a transferase, a hydrolase, a lyase, an isomerase, or a ligase; and
optionally, a cofactor.

5. The method of claim 4, wherein the biocatalyst is immobilized to the polymer through an amide bond.

6. The method of claim 5, wherein the hydrophobic group is an optionally substituted C8–C30 alkyl, polycyclic alkyl, polycyclic aryl, or polycyclic heteroaryl, or a C8–C30 alkyl optionally interrupted by a cyclic or polycyclic alkyl, aryl, or heteroaryl.

7. The method of claim 6, wherein the polymer is substantially adhered to the flow surface by hydrophobic interactions, electrostatic interactions, or by a covalent bond.

8. The method of claim 7, wherein the polymer is substantially adhered to the flow surface by covalent attachment.

9. The method of claim 8, wherein the polymer is covalently attached to the flow surface through a linker comprising an amide bond.

10. The method of claim 9, wherein the polymer is covalently attached to the flow surface through a linker represented by structural formula B:

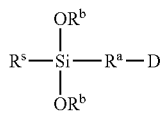

B wherein
the surface comprises an —Si—O— group represented by $R^s$;
each $R^b$ is independently a C1–C4 alkyl group;
$R^a$ is a C1–C8 alkylene chain; and
D represents an amide bond to the polymer.

11. The method of claim 10, further comprising the steps of
directing a second biocatalyst from a source to the polymer, wherein the second biocatalyst is catalytically distinct from the first biocatalyst;
reacting the second biocatalyst with the biomolecule-immobilizing group under suitable reaction conditions, whereby the second biocatalyst is immobilized.

12. The method of claim 11, wherein the second biocatalyst is immobilized by the polymer at a second flow surface that is spatially distinct from the first flow surface, whereby the first and the second biocatalysts are catalytically and spatially distinct.

13. The method of claim 12 wherein the polymer is represented by a structure derived from a copolymer of ethylenically unsaturated monomers, wherein the monomers are substituted with groups selected from the ionic groups and precursors thereof, the hydrophobic groups, the biomolecules, and the linker.

14. The method of claim 13, wherein
the ionic groups are selected from carboxylate, carbamate, sulfate, thiosulfate, sulfonate, phosphate, phosphonate, and hydroxyl;
the precursor groups are selected from optionally substituted alkyl esters, alkyl anhydrides, cyclic anhydrides, alkyl ethers, aryl esters, aryl anhydrides, and aryl ethers of the ionic groups.

15. The method of claim 14, further comprising the step of reacting the precursor groups under suitable reaction conditions, thereby forming the ionic groups.

16. The method of claim 15, wherein the polymer is a maleic anhydride-α-olefin polymer derivative, wherein
the ionic groups consists of carboxylate derived from a maleic anydride monomer;
the hydrophobic group is a C12–C28 alkyl chain;
the biocatalysts are each immobilized through an amide bond to a carboxyl derived from a maleic anhydride monomer;
the amide bond represented by D comprises a carboxyl derived from a maleic anhydride monomer.

17. The method of claim 13, wherein the ionic groups are selected from ammonium, phosphonium, and sulfonium groups optionally substituted with one or more groups selected from C1–C8 alkyl and aryl.

18. A method for conducting one or more reactions by employing electroosmotic flow, comprising the steps of:
a) providing a microfluidic biochip, comprising
a plurality of microfluidic components, wherein
at least one said component comprises a flow surface;
at least one said component is a reservoir, wherein the reservoir contains a starting reactant;
the components are in microfluidic communication;
a plurality of electrodes, whereby an electroosmotic flow can be generated at the flow surface;
an immobilizing polymer coated on the surface, wherein the polymer is substantially adhered to the surface, the polymer comprising a backbone to which are attached
a first substituent selected from ionic groups of the same polarity;
a second substituent that is a hydrophobic group;
a first biomolecule covalently bound to the first substituent of the immobilizing polymer; and
an optional second immobilized biomolecule covalently bound to the first substituent of the immobilizing polymer, wherein the second biomolecule is chemically distinct from the first biomolecule;
b) applying a voltage to the electrodes, thereby generating electroosmotic flow;
c) directing a first reactant from the reservoir to the first immobilized biomolecule by employing the electroosmotic flow, and reacting the first reactant with the first biomolecule under suitable reaction conditions, thereby producing a first reaction product; and
d) optionally contacting the first reaction product with the second immobilized biomolecule, if present; and reacting the first reaction product with the second biomolecule under suitable reaction conditions, thereby producing a second reaction product.

19. The method of claim 18, wherein at least one said microfluidic component is a microchannel, wherein a cross-sectional area of the microchannel is less than about 0.1 mm².

20. The method of claim 19, wherein
the polymer is coated on at least two spatially distinct flow surfaces;
the first and second biomolecules are separately immobilized on the polymer coated at the distinct flow surfaces, whereby the first and second biomolecules are chemically and spatially distinct.

21. The method of claim 20, wherein each said chemically distinct biomolecule is a catalytically distinct biocatalyst, comprising
a catalytically functional portion of an antibody, an enzyme, a peptide, or an oligonucleotide; and
optionally, a cofactor.

22. The method of claim 21, wherein each said catalytically distinct biocatalyst comprises
a catalytically functional portion of an oxidoreductase, a transferase, a hydrolase, a lyase, an isomerase, or a ligase; and
optionally, a cofactor.

23. The method of claim 22, wherein the hydrophobic group is an optionally substituted C8–C30 alkyl, polycyclic alkyl, polycyclic aryl, or polycyclic heteroaryl, or a C8–C30 alkyl optionally interrupted by a cyclic or polycyclic alkyl, aryl, or heteroaryl.

24. The method of claim 23, wherein the polymer is substantially adhered to each said flow surface by hydrophobic interactions, electrostatic interactions, or by a covalent bond.

25. The method of claim 24, wherein the polymer is substantially adhered to each said flow surface by covalent attachment.

26. The method of claim 25, wherein each said biocatalyst is immobilized to the polymer through an amide bond.

27. The method of claim 26, wherein the polymer is covalently attached to the flow surface through a linker comprising an amide bond.

28. The method of claim 27, wherein the polymer is covalently attached to the flow surface through a linker represented by structural formula B:

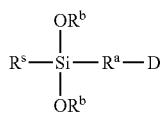

B wherein
the surface comprises an —Si—O— group represented by $R^s$;
each $R^b$ is independently a C1–C4 alkyl group;
$R^a$ is a C1–C8 alkylene chain; and
D represents an amide bond to the polymer.

29. The method of claim 28, wherein the polymer is represented by a structure derived from a copolymer of ethylenically unsaturated monomers, wherein the monomers are substituted with groups selected from the ionic groups, the hydrophobic groups, the biocatalysts, and the linker.

30. The method of claim 29, wherein the ionic groups are selected from carboxylate, carbamate, sulfate, thiosulfate, sulfonate, phosphate, phosphonate, and hydroxyl.

31. The method of claim 30, wherein the polymer is a maleic anhydride-α-olefin polymer derivative, wherein
the ionic groups consist of carboxylate derived from a maleic anydride monomer;
the hydrophobic substituent is a C12–C28 alkyl chain;
the biocatalysts are each immobilized through an amide bond to a carboxyl derived from a maleic anhydride monomer;

the amide bond represented by D comprises a carboxyl derived from a maleic anhydride monomer.

32. The method of claim 29, wherein the ionic groups are selected from ammonium, phosphonium, and sulfonium groups substituted with one or more groups selected from C1–C8 alkyl and aryl.

33. A microfluidics biochip, comprising:
a) at least one microfluidic reservoir;
b) a plurality of microfluidic channels, wherein
the channels are each less than about 0.1 mm² in cross-sectional area;
the channels each comprise a flow surface, wherein
a polymer is coated on at least one said flow surface, wherein the polymer is substantially adhered to the surface, wherein the polymer comprises a backbone to which are attached
one or more ionic substituents of the same polarity selected from optionally substituted carboxylate, carbamate, sulfate, thiosulfate, sulfonate, phosphate, phosphonate, or hydroxyl;
one or more hydrophobic substituents selected from optionally substituted C8–C30 alkyl, a polycyclic alkyl, or a polycyclic aryl; and
at least two catalytically distinct biocatalysts that are each immobilized to the polymer through an amide bond;
the channels are in microfluidic communication with each other and with the reservoir;
each said channel is in microfluidic communication with at least two electrodes, whereby an electroosmotic flow can be generated at the flow surfaces;
whereby an electroosmotic flow can be generated to direct
a reactant solution from the reservoir to a first said catalytically distinct biocatalyst, whereby a first reaction product can be produced; and
the first product from the first biocatalyst can be contacted with a to a second said catalytically distinct biocatalyst, whereby a second reaction product can be produced.

34. The biochip of claim 33, further comprising
at least two spatially distinct flow surfaces, wherein
the flow surfaces are in microfluidic communication;
the flow surfaces are coated with the polymer;
at least two said catalytically distinct enzymes are respectively immobilized to the polymer at the spatially distinct flow surfaces; and
whereby the biocatalysts are catalytically and spatially distinct.

35. The biochip of claim 34, wherein the polymer is substantially adhered to the flow surface by hydrophobic interactions, electrostatic interactions, or by a covalent bond.

36. The biochip of claim 34, wherein the polymer is covalently attached to the flow surface through a structure represented by formula B:

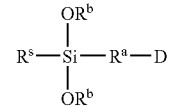

B wherein
the surface comprises an —Si—O— group represented by $R^s$;
$R^a$ is a C1–C8 alkylene chain;
each $R^b$ is independently a C1–C4 alkyl group; and
D represents an amide bond to the polymer.

* * * * *